United States Patent
Peng et al.

(10) Patent No.: US 9,429,607 B2
(45) Date of Patent: Aug. 30, 2016

(54) LOW GDS MEASUREMENT METHODOLOGY FOR MOS

(71) Applicant: Taiwan Semiconductor Manufacturing Co., Ltd., Hsin-Chu (TW)

(72) Inventors: Yung-Chow Peng, Hsinchu (TW); Po-Zeng Kang, Hsin-Hua (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 300 days.

(21) Appl. No.: 14/107,140

(22) Filed: Dec. 16, 2013

(65) Prior Publication Data

US 2015/0168468 A1     Jun. 18, 2015

(51) Int. Cl.
| | | |
|---|---|---|
| G01R 27/08 | (2006.01) | |
| G01R 31/26 | (2014.01) | |
| G01N 27/02 | (2006.01) | |

(52) U.S. Cl.
CPC ........... *G01R 27/08* (2013.01); *G01R 31/2621* (2013.01); *G01N 27/025* (2013.01)

(58) Field of Classification Search
None
See application file for complete search history.

(56) References Cited

U.S. PATENT DOCUMENTS

| | | | | |
|---|---|---|---|---|
| 5,570,049 | A * | 10/1996 | Chen | H03F 1/3211 327/103 |
| 6,977,553 | B1* | 12/2005 | Jin | H03G 1/0029 330/285 |
| 7,220,677 | B2 | 5/2007 | Li et al. | |
| 8,115,553 | B1* | 2/2012 | Wang | H03F 1/26 330/264 |
| 2007/0109026 | A1* | 5/2007 | Ho | H03K 5/2481 327/65 |
| 2011/0063030 | A1* | 3/2011 | Jang | H03F 3/45188 330/254 |
| 2012/0038423 | A1* | 2/2012 | Zhou | H03F 1/223 330/277 |
| 2012/0176193 | A1* | 7/2012 | Chiang | H01L 23/4824 327/566 |
| 2012/0286747 | A1* | 11/2012 | Chen | H02M 1/32 323/271 |

OTHER PUBLICATIONS

Graf, Rudolf F. (1999). Modern Dictionary of Electronics (7 ed.). Newnes. p. 314.*

* cited by examiner

*Primary Examiner* — Melissa Koval
*Assistant Examiner* — Felicia Farrow
(74) *Attorney, Agent, or Firm* — Eschweiler & Associates, LLC

(57) ABSTRACT

A dummy MOSFET is connected in series with a device under test to form cascode structure. The conductance of the low conductance MOSFET is derived from the measurements done on the cascode structure. An open loop gain stage is connected to the cascode structure in case the signal at the internal node of the cascode structure is extremely small to be measured directly and accurately. Impedance measurements can also be done on high impedance MOS devices without noise distortion with the help of the cascode arrangement.

18 Claims, 5 Drawing Sheets

LOW GDS MEASUREMENT METHODOLOGY FOR MOS

BACKGROUND

The size of semiconductor devices has been continuously shrinking since the introduction of semiconductor devices, resulting in smaller semiconductor chip size and increased device density. Reliability and electrical continuity of integrated circuitry wiring is determined by electrical continuity measurement methods following formation of metallization level of circuitry wiring, also referred to as wafer acceptance testing (WAT). In semiconductor fabrication processes, the WAT is usually performed to test some wafers after some manufacturing processes. Some sample wafers are tested by a WAT tool (measuring equipment) so that a WAT value associated with the manufacturing process is obtained. Normally the test structures are comprised of single transistors, resistors, capacitors, and other passive structures. Basic electrical parameters signify whether the die located on the wafer can normally operate or not. Thus, the electrical parameters which are measured need to match the original predetermined electrical parameters, and the abnormal basic electrical parameters reflect the problems on manufacturing line. Conductance (gds) is one analog parameter of WAT. Electrical conductance is the ease with which current passes through a circuit.

DETAILED DESCRIPTION

Figure 1:
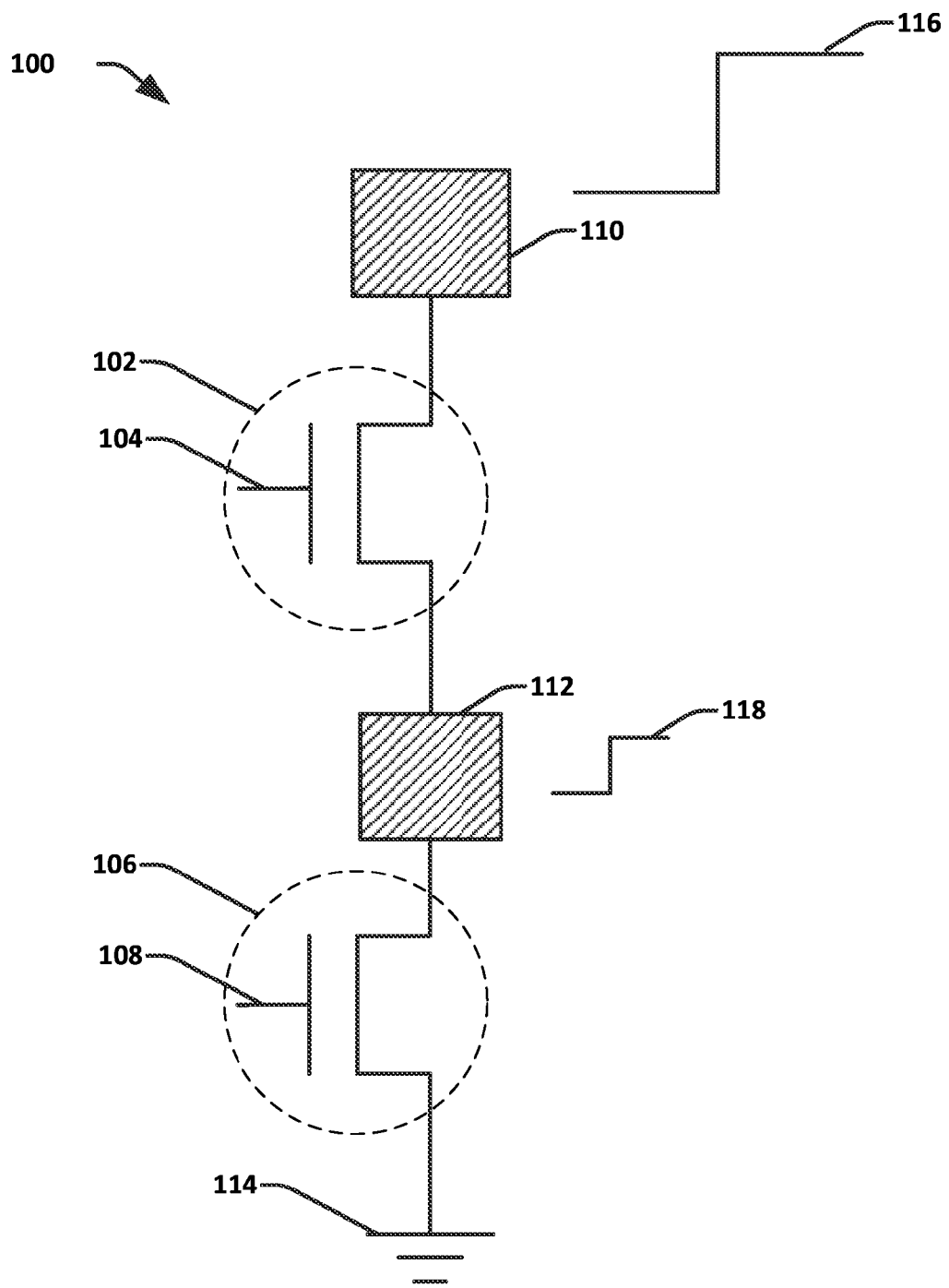
FIG. 1 is a circuit diagram of a cascode structure with the device under test as one of the transistors.

Some aspects of the present disclosure relate to a methodology for characterizing low conductance MOS devices by introducing a cascode structure.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

As mentioned, conductance (gds) is one analog parameter of wafer acceptance testing (WAT), and it is directly related, and very nearly linear with, timed-discharge capacity of the device. However, at lower conductance values (e.g., <1e-6 Mho), the accuracy of conventional WAT systems deteriorate. It is desirable for the whole device to be characterized accurately to make analog gain and conductance at the corners of the device accurate. A novel solution to the above mentioned limitation is provided herein that can push measurement accuracy of the WAT conductance value to ~1e-8 Mho.

As the semiconductor size keeps decreasing, the impedance of the MOS device keeps increasing. For a MOS device with gate length (Lg) larger than 1 um (micro meter), the device impedance will be close to or larger than 1e7 Ohm. If the impedance of the device under test was to be measured directly from the output node, the variation in the output would be high due to the sensitivity of the high impedance output node to noise. Furthermore, there is a limit to the maximum value of impedance that could be derived using this direct measurement method. In some embodiments, the direct measurement method for calculating the impedance includes sweeping an input voltage, measuring the corresponding output current and dividing the change in voltage by the output change in current. In other words, if the change in current versus swept voltage is plotted for a device, the slope of the graph would give the impedance of that device. For a minimum output swing of ~0.1V, the maximum current change observed was 100 nA and hence the maximum impedance that could be derived from this method was ~1e6 Ohm. This method limits the current accuracy of the measured results since the bias current of MOS devices is at a few micro amperes (μA).

In the present disclosure, a serial gate or cascode structure is formed with two MOS devices, one being the device under test and the other a dummy MOS device coupled in series. In some embodiments, the cascode device comprises an output node which is also the drain terminal of the device under test and an internal node at which the two MOS devices are connected in series. According to the present disclosure, conductance (gds) of the device under test can be derived from the gain of the cascode structure (G) and the transconductance (gm) of the device under test (which will be discussed in detail later).

For a serial gate or cascode structure, the output impedance can be derived by multiplying the gain of the cascode structure and the impedance of the first MOS device. i.e., If M1 and M2 respectively are the first and second MOS devices that form a cascode structure, Zout (M1+M2) is the impedance of the cascode structure (the impedance across the output node and ground), G is the gain of the cascode device, Zout (M2) is the impedance of the second MOS device and Zout (M1) is the impedance of the first MOS device, and gm (M2) is the trans-conductance of the second MOS device, then:

$$Zout(M1+M2) = Zout(M2) + Zout(M1) + gm(M2) * Zout(M2) * Zout(M1) \quad (1)$$
$$= \sim gm(M2) + Zout(M2)*Zout(M1)$$
$$= G*Zout(M1)$$

and $$Zout(M1) = Zout(M1+M2)/((Zout(M2)*gm(M2))) \quad (2)$$

where $G(M2)=gm(M2)*Zout(M2)$ is the gain of the second MOS device.

However for a single high impedance MOS device, since it is difficult to directly measure the accurate impedance value from the output node due to sensitivity to noise, an efficient solution according to the present disclosure is to modify the single high impedance MOS device into a cascode structure by adding a dummy low impedance MOS device and calculating the impedance by applying the above described formula. This method can cover extremely low gds because a signal at a high impedance node can be transferred and attenuated to proper level. Furthermore, a fast and accurate measurement can be made since there will be no high impedance sensitive node involved in the measurements.

FIG. 1 shows the circuit diagram of a cascode structure 100 according to some embodiments of the present disclosure. The cascode structure has a first MOSFET device or device under test (DUT) 102 and a second MOSFET device 106, which is a dummy device added to the first MOSFET 102. 104 represents a first gate contact associated with a gate of the first MOSFET device and 108 represents a second gate contact associated with a gate of the second MOSFET device. The cascode structure has an output node 110 which is also a drain terminal of the transistor 102 and an internal node 112 at a middle location of the cascode structure which is also a source terminal of the device under test 102. The ground terminal of the cascode structure is represented by 114. During device characterization, a predetermined value of voltage is applied at the output node 110 and that voltage signal or the change in voltage at the output node 110 is represented by 116. The dummy transistor or second MOSFET device 106 connected to the first MOSFET device 102 that forms the cascode structure will attenuate the signal applied at the output node and the corresponding voltage change at the source of the first MOSFET device or the internal node of the cascode structure is represented as 118.

The cascode structure in the present disclosure helps derive different parameters that cannot be measured accurately by direct measurement methodologies. In some embodiments, the conductance (gds(M1)) of the first MOSFET could be derived by dividing the transconductance (gm(M1)) of the first MOSFET by the gain of the cascode structure (G). i.e., $$gds(M1)=gm(M1)/G \quad (3)$$

In some embodiments calculating the gain of the cascode structure comprises sweeping the voltage at the output node 110 by a predetermined amount, for e.g., say by ΔV1, measuring the corresponding change in voltage at the internal node 112, for e.g., say ΔV2, and dividing ΔV1 by ΔV2. i.e., $$G=\Delta V1/\Delta V2 \text{ or } (\Delta V2/\Delta V1)^{-1}. \quad (4)$$

According to some embodiments of the present disclosure, calculating the transconductance (gm) of the first MOSFET comprises the following. Short the internal node 112 to ground, maintain a voltage at the gate 104 (for e.g., say Vg1) of the first MOSFET device, apply a voltage ΔV1 to node 110, measure an output current at the same node and divide the change in output current at the output node by the change in voltage at the output node. i.e., if ΔI1 is the change in output current at the internal node 112, then:

$$gm(M1)=\Delta I1/\Delta V1. \quad (5)$$

Thus, conductance (gds) of the device under test can be derived using equations (4) and (5) in equation (3).

As described previously, the impedance of the device under test can be derived using the impedance of the cascode structure, gain of the cascode structure and the impedance of the second dummy MOS device. In some embodiments, during impedance measurement of the second MOSFET, the first MOSFET has to be turned off (e.g., by making Vg1=0). Further, the impedance of the second MOSFET 106 is calculated by sweeping the voltage at the internal node 112, measuring the current at the internal node 112 and dividing the change in voltage at node 112 by the change in current at node 112. i.e., if ΔV2 is the change in voltage and ΔI2 is the change in current both at the internal node 112, then $$Zout(M2)=\Delta V2/\Delta I2. \quad (6)$$

Thus impedance of the cascode structure can be derived using equations (4) and (6) in equation (1) and the result of (1) can be used in equation (2) to calculate the impedance of the device under test.

In some embodiments, the gain of the cascode structure is also equal to the product of the transconductance and impedance of the device under test. i.e., $$G=gm(M1)*Zout(M1). \quad (7)$$

Thus, the impedance of the device under test could also be derived using the formula:

$$Zout(M1)=G/gm(M1). \quad (8)$$

Figure 2:
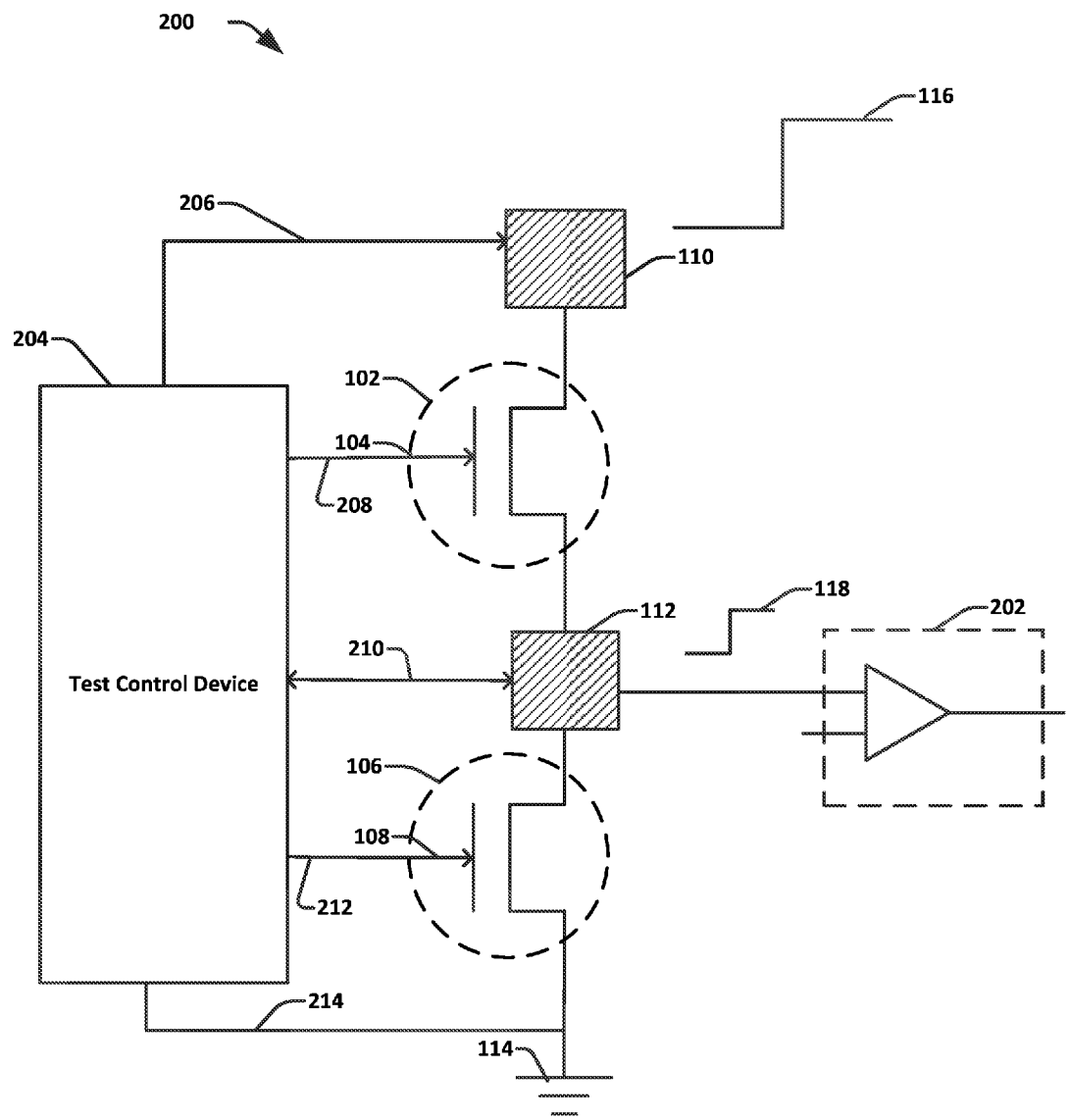
FIG. 2 is a circuit diagram of a cascode structure with an open loop gain stage connected to an internal node of the cascode structure.

FIG. 2 illustrates some embodiments of a measurement tool 200 configured to characterize a low gds MOSFET device according to the present disclosure. During operation, voltages and currents need to be applied and measured at both the output node 110 and the internal node 112 of the cascode structure. In one embodiment, a test control device 204 performs the sourcing and measuring on the cascode structure. 208 represents an output line of the test control device 204 that supplies a voltage Vg1 to the gate contact 104 of the first MOSFET device 102. 212 is another source line of the test control device that supplies a voltage Vg2 to the gate contact 108 of the second MOSFET device 106. There is a two way source measure unit (SMU) 210 on the test control device 204 that can supply and measure both current and voltage at the internal node 112 of the cascode structure. 206 is another source measure unit that supplies and measures voltages and currents at the output node 110. 214 represents the terminal that is grounded. If the output signal at the internal node 112 is really small, it may be difficult to be measured directly by the test control device and a separate amplifying circuit will be required to boost the signal at node 112. In such a case, an open loop gain stage 202 connected to the internal node 112 becomes active and the amplified output signal of node 112 can be measured at the output terminal of the open loop gain stage.

Figure 3:
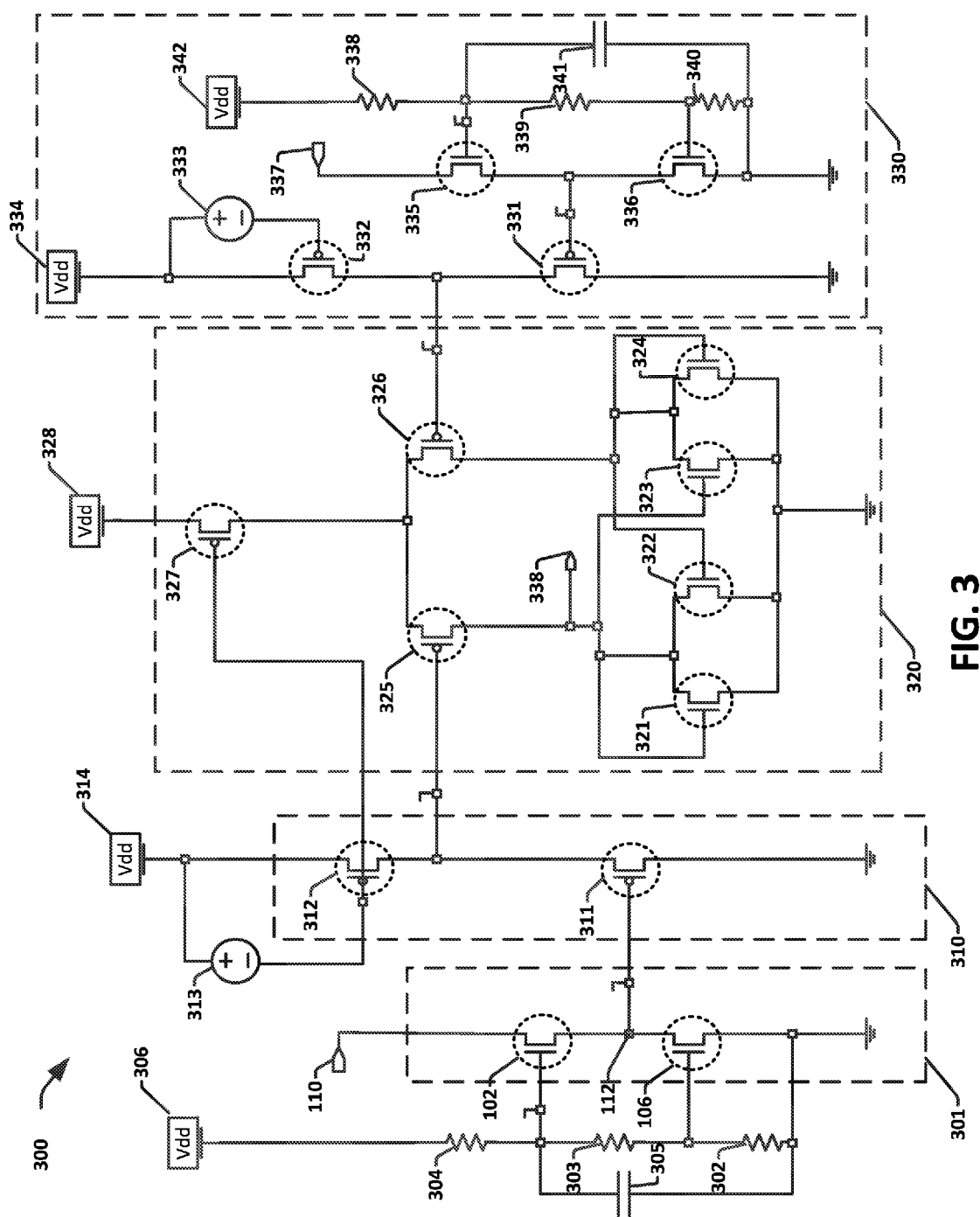
FIG. 3 is a circuit diagram of the cascode structure, a buffer stage, an open loop gain stage and a mirror circuit that are all connected in series.

FIG. 3 illustrates a circuit diagram 300 according to some embodiments of the present disclosure wherein the cascode structure is connected to an open loop gain stage through a buffer circuit. Here, 301 represents the cascode structure with the device under test 102 and the dummy second MOS device 106. The MOS devices of the cascode structure are connected to a voltage divider set up comprising resistors and a capacitor. In the figure, they are represented by resistor 302, resistor 303, resistor 304 and capacitor 305. They divide and control the dc bias voltage coming from the bias supply 306 to the MOS devices. Connected to the cascode structure 301 is a buffer circuit 310, which alters the dc level and makes the output of the device under test match with an open loop gain stage 320. The buffer stage 310 is connected in series with the cascode structure 301 through the internal node 112. The buffer stage 310 comprises two p-MOS transistors 311 and 312, a voltage source 313 connected to the gate of 312 and a DC voltage supply 314 connected to the drain of 312. Transistor 312 acts like a switch and decides whether the signal coming from node 112 needs to be sent to the open loop gain stage or not. The open loop gain stage 320 comprises two differential amplifier stages formed by n-MOS transistor pairs (321,322) and (323,324) whose outputs are connected with opposite phases of their inputs. The inputs of these amplifier stages are fed from outputs of a third differential pair, formed by p-MOS transistor pairs 325 and 326. Combining the two difference stages, output current yields four-quadrant operation. Thus the open loop gain stage acts as a four-quadrant multiplier that can boost the signal at the internal node 112 to approximately 5 to 10 times its initial value and the amplified output is received at the output node 338 of the open loop gain stage. The open loop gain stage also comprises a p-MOS transistor 327 that acts as a current source and a DC bias supply 328 connected to the source of 327. Attached to the gate of the p-MOS transistor 326 is a mirror circuit 330. The mirror circuit is designed to copy the current going into p-MOS transistor 325 and provide the same current with opposite phase as the input of 326 so that the outputs of 325 and 326 are kept constant regardless of loading. In other words, the current mirror or the mirror circuit is an ideal inverting current amplifier that reverses the current direction and provide bias currents for the proper functioning of the four-quadrant amplifier stages of the open loop gain stage. The mirror circuit 330 comprises all the components of the cascode stage 301 and the buffer stage 310 in reverse direction. It comprises two n-MOS transistors 335 and 336 that mirror transistors 102 and 106 respectively. A voltage divider set up comprising 3 resistors (338, 339 and 340) and a capacitor 341 that divides and controls the voltage coming from the DC supply 342 is also present. A voltage bias having a magnitude that is equal to the middle of the swept voltage at the external node 110 of the first MOSFET device is supplied to node 337. Two p-MOS transistors 331 and 332 that mirror transistors 311 and 312 and a DC bias supply 334 and a voltage source 333 completes the mirror circuit 330.

Figure 4:
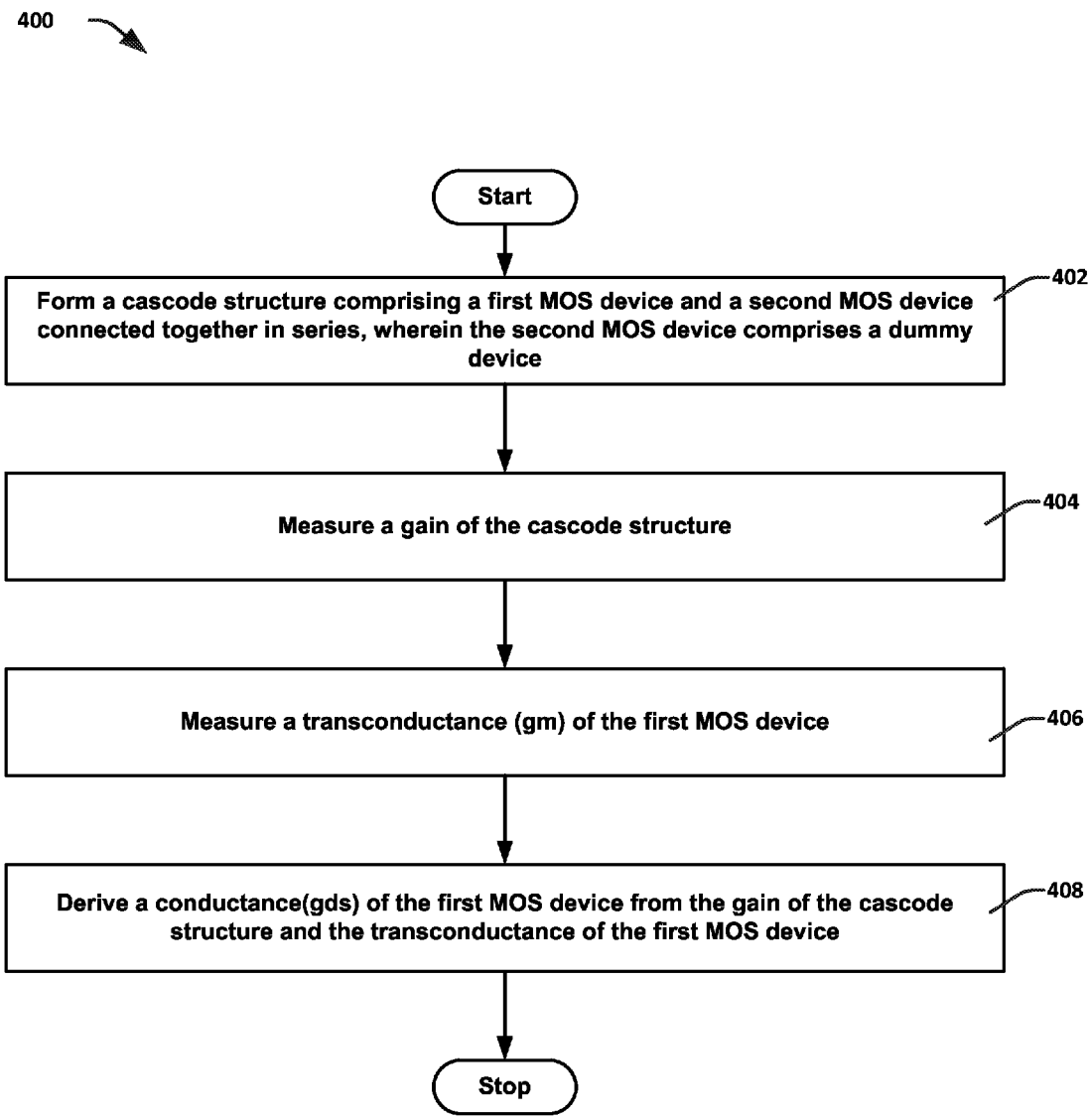
FIG. 4 shows a flow diagram of a method according to some embodiments of the present disclosure.

FIG. 4 illustrates a flow diagram of some embodiments of a method 400 for measuring the conductance of a low conductance MOSFET device according to various embodiments of the disclosure. While method 400 is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 402, a cascode structure is formed by connecting a second MOS device to the first MOS device, wherein the second MOS device is a low impedance dummy device. The first MOS device is the low conductance device under test. One example of such an arrangement is illustrated in FIG. 1.

At 404, the gain of the cascode structure is measured. In one embodiment, this is accomplished by sweeping a predetermined amount of voltage at the output node, measuring the corresponding change in voltage at the internal node and dividing the former by the latter.

At 406, a transconductance (gm) of the first MOS device is measured. The calculation for transconductance of the first MOS device comprises shorting the internal node to ground, maintaining the voltage at the gate of the first MOS device, applying a voltage to the output node, measuring the output current at the same node and dividing the change in output current by the change in voltage both at the output node.

At 408, the conductance (gds) of the first MOS device is derived by dividing the transconductance of the first MOS device by the gain of the cascode structure.

Figure 5:
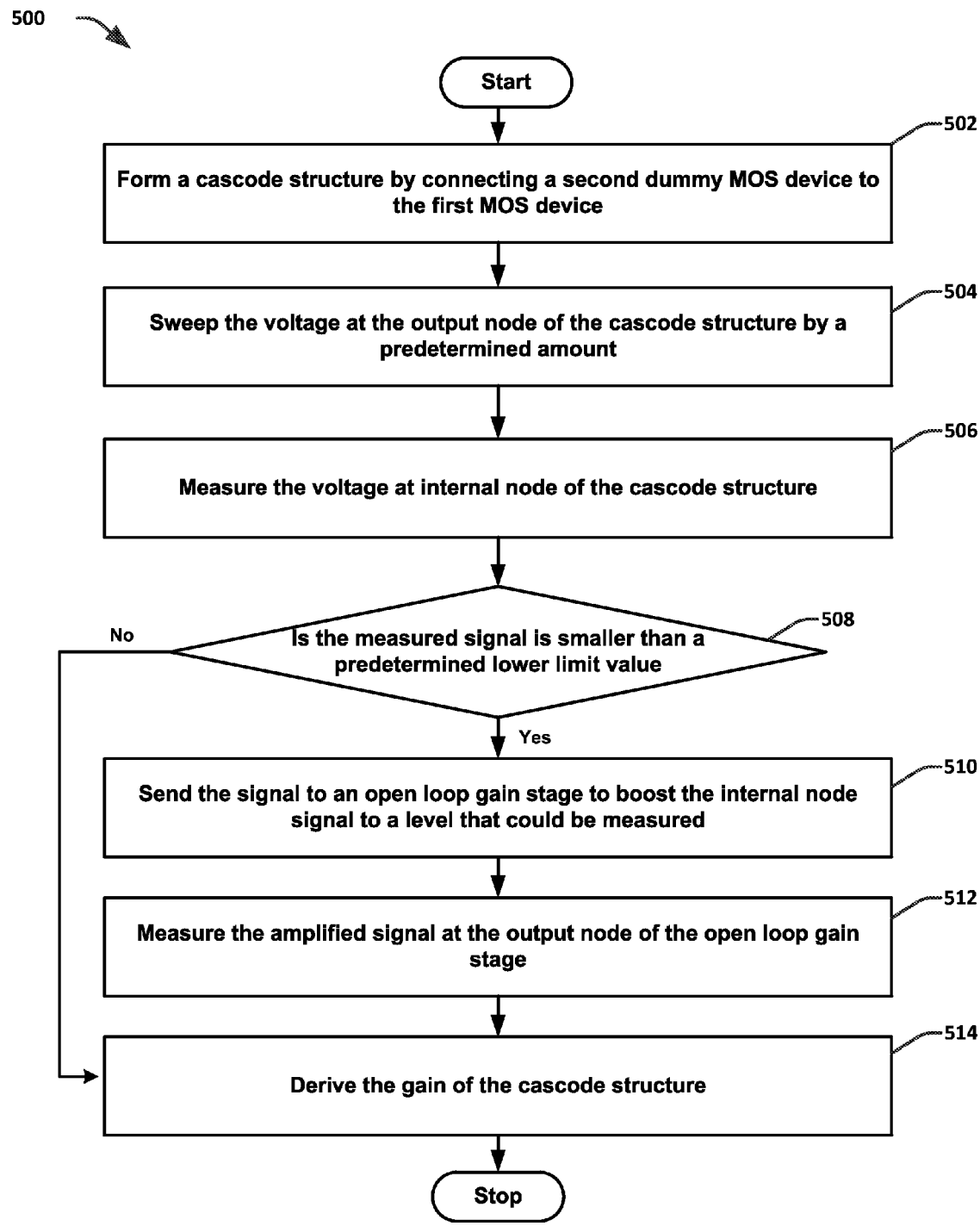
FIG. 5 shows a flow diagram of a method to calculate gain of the cascode structure according to some embodiments of the present disclosure.

FIG. 5 illustrates a flow diagram of some embodiments of a method 500 for deriving the gain of a cascode structure according to various embodiments of the disclosure. While method 500 is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 502, a cascode structure is formed by connecting a second MOS device to the first MOS device or the device under test, for example, as illustrated in FIG. 1.

At 504, a predetermined amount of voltage is swept at the output node of the cascode structure.

At 506, the corresponding change in voltage is measured at the internal node of the cascode structure.

At 508, the measured signal at the internal node is compared to a predetermined low limit value. For MOS devices with extremely low gds, the signal at the internal node would be extremely small and in some circumstances may not be measured accurately using direct measurement methodologies. The low limit value comprises a value such that below that predetermined limit value, the accuracy of the measured signal is unreliable.

If the signal measured at the internal node is found to be smaller than the predetermined low limit value (YES at 508), then step 508 is followed by step 510, wherein the signal at the internal node is sent to an open loop gain stage so that it is amplified to a level that could be measured.

If the signal measured at the internal node is found to be higher than the predetermined low limit value (NO at 508), then step 508 will proceed to 514 where the gain of the cascode structure is derived using the measured signal.

At 512, the amplified signal having a higher gain is measured at the output node of the open loop gain stage.

At 514, the gain of the cascode structure is derived with the accurate signal value which is derived from the output of the open loop gain stage.

It will be appreciated that while reference is made throughout this document to exemplary structures in discussing aspects of methodologies described herein, those methodologies are not to be limited by the corresponding structures presented. Rather, the methodologies and structures are to be considered independent of one another and able to stand alone and be practiced without regard to any of the particular aspects depicted in the Figs. Additionally, layers described herein can be formed in any suitable manner, such as with spin on, sputtering, growth and/or deposition techniques, etc.

Also, equivalent alterations and/or modifications may occur to one of ordinary skill in the art based upon a reading and/or understanding of the specification and annexed drawings. The disclosure herein includes all such modifications and alterations and is generally not intended to be limited thereby. For example, although the figures provided herein are illustrated and described to have a particular doping type, it will be appreciated that alternative doping types may be utilized as will be appreciated by one of ordinary skill in the art.

In addition, while a particular feature or aspect may have been disclosed with respect to one of several implementations, such feature or aspect may be combined with one or more other features and/or aspects of other implementations as may be desired. Furthermore, to the extent that the terms "includes", "having", "has", "with", and/or variants thereof are used herein, such terms are intended to be inclusive in meaning—like "comprising." Also, "exemplary" is merely meant to mean an example, rather than the best. It is also to be appreciated that features, layers and/or elements depicted herein are illustrated with particular dimensions and/or orientations relative to one another for purposes of simplicity and ease of understanding, and that the actual dimensions and/or orientations may differ from that illustrated herein.

Therefore, the present disclosure relates to an efficient methodology for fast and accurate measurement of conductance on extremely low conductance MOSFET devices. A second MOSFET device having low impedance is connected with the device under test to form a cascode structure. The measurements done on the cascode structure helps derive low conductance, high impedance etc. that cannot be measured directly with accuracy.

In some embodiments the present disclosure relates to a method of low conductance (gds) measurement on a single metal-oxide-semiconductor (MOS) device which is under test, the method comprising, forming a cascode structure comprising a first MOS device and a second MOS device connected together in series, wherein the second MOS device comprises a dummy device, measuring a gain of the cascode structure, measuring a transconductance (gm) of the first MOS device and deriving a conductance of the first MOS device from the gain of the cascode structure and the transconductance of the first MOS device.

In some embodiments the present disclosure relates to a method of characterizing a high impedance or low conductance metal oxide semiconductor field effect transistor (MOSFET) which is under test, the method comprising, forming a cascode structure by connecting a first MOSFET device and a second MOSFET device together in series, wherein the second MOSFET device comprises a dummy device and the cascode structure comprises an output node at one end location of the first MOSFET, an internal node at a middle location of the cascode structure where the first MOSFET couples to the second MOSFET, a first gate contact associated with a gate of the first MOSFET device configured to receive a gate voltage Vg1 and a second gate contact associated with a gate of the second MOSFET device configured to receive a gate voltage Vg2, measuring a gain of the cascode structure by dividing a change in a voltage at the output node by a change in a voltage at the internal node, measuring a transconductance (gm) of the first MOSFET device by shorting the internal node to ground, maintaining a voltage at the gate of the first MOSFET device and dividing an output current by a voltage at the output node and deriving a conductance of the first MOSFET device by dividing the gain of the cascode structure by the transconductance of the first MOSFET device.

In some embodiments, the present disclosure relates to a test control device, comprising, a first voltage source attached to a gate of a first MOSFET device, a second voltage source attached to a gate of a second MOSFET device, a source measure unit (SMU) which is connected to an output node of the first MOSFET device and an SMU that is connected to an internal node of a cascode structure.

What is claimed is:

1. A method for measuring the conductance of a low conductance metal oxide semiconductor (MOS), the method comprising:

forming a cascode structure comprising a first MOS device and a second MOS device connected together in series, an output node, an internal node that couples the first MOS device to the second MOS device, a first gate contact associated with a gate of the first MOS device configured to receive a gate voltage Vg1, and a second gate contact associated with a gate of the second MOS device configured to receive a gate voltage Vg2, the second MOS device comprising a dummy device, wherein the first MOS is connected to an open loop gain stage when a signal at the internal node is smaller than a predetermined low limit value, and wherein the predetermined low limit value identifies a minimum signal reliability threshold;

measuring a gain of the cascode structure;

measuring a transconductance (gm) of the first MOS device; and deriving a conductance (gds) of the first MOS device from the gain of the cascode structure and the transconductance of the first MOS device.

2. The method of claim 1, further comprising:

measuring an impedance of the second dummy MOS device; and deriving an impedance of the cascode structure from the impedance of the second dummy MOS device and the gain of the cascode structure.

3. The method of claim 1, further comprising deriving an impedance of the first MOS device by dividing the gain of the cascode structure by the transconductance of the first MOS device.

4. The method of claim 1, the measuring of the transconductance (gm) of the first MOS device comprising:

maintaining a voltage at the gate of the first MOS device; and dividing an output current by a voltage at the output node.

5. The method of claim 1, the measuring of the gain of the cascode structure comprising dividing a change in a voltage at the output node of the cascode structure by a change in a voltage at the internal node of the cascode structure.

6. The method of claim 2, the measuring of the impedance of the second dummy MOS device comprising:

turning off the first MOS device;

sweeping a voltage at the internal node by a predetermined amount;

measuring a change in current across the second MOS device in response to the swept voltage; and dividing the predetermined amount of the swept voltage by the change in current.

7. The method of claim 2, the impedance of the cascode structure derived by multiplying the gain of the cascode structure with the impedance of the second dummy MOS device.

8. The method claim 1, the conductance of the first MOS device derived by dividing the transconductance of the first MOS device by the gain of the cascode structure.

9. A method of characterizing a high impedance or low conductance metal oxide semiconductor field effect transistor (MOSFET) under test, the method comprising:

forming a cascode structure by connecting a first MOSFET device and a second MOSFET device together in series the second MOSFET device comprises a dummy device and the cascode structure comprises an output node at one end location of the first MOSFET, an internal node at a middle location of the cascode structure where the first MOSFET couples to the second MOSFET, a first gate contact associated with a gate of the first MOSFET device configured to receive a gate voltage Vg1 and a second gate contact associated with a gate of the second MOSFET device configured to receive a gate voltage Vg2;

connecting an open gain stage to the first MOSFET device when a signal at the internal node is smaller than a predetermined low limit value, wherein the predetermined low limit value identifies a minimum signal reliability threshold;

measuring a gain of the cascode structure by dividing a change in a voltage at the output node by a change in a voltage at the internal node;

measuring a transconductance (gm) of the first MOSFET device, maintaining a voltage at the gate of the first MOSFET device and dividing an output current by a voltage at the output node; and deriving a conductance of the first MOSFET device by dividing the gain of the cascode structure by the transconductance of the first MOSFET device.

10. The method of claim 9, further comprising:

measuring an impedance of the second MOSFET device by turning off the first MOSFET device, sweeping a voltage at the internal node by a predetermined amount, measuring a change in current across the second MOSFET device and dividing the predetermined amount of the swept voltage by the change in current; and deriving an impedance of the cascode structure by multiplying the gain of the cascode structure with the impedance of the second MOSFET device.

11. The method of claim 9, further comprising attaching a buffer stage to the internal node, connecting the cascode structure and the open loop gain stage.

12. The method of claim 9, further comprising attaching a mirror circuit to an input of a PMOS transistor of a differential pair in the open loop gain stage.

13. The method of claim 9, the open loop gain stage amplifying the signal at the internal node to approximately 5 to 10 times.

14. The method of claim 12, further comprising supplying to the mirror circuit a bias voltage having a magnitude that is equal to a voltage at the middle of the swept voltage at the internal node of the first MOSFET device.

15. A test control device, comprising:

a first voltage source attached to a gate of a first MOSFET device;

a second voltage source attached to a gate of a second MOSFET device;

a source measure unit (SMU) which is connected to an output node of the first MOSFET device; and a source measure unit which is connected to an internal node of a cascode structure, wherein the first MOSFET device is connected to an open loop gain stage when a signal at the internal node is smaller than a predetermined low limit value, and wherein the predetermined low limit value identifies a minimum signal reliability threshold.

16. The device of claim 15, the SMU connected to the output node configured to sweep the voltage at the output node and measure a corresponding response current at the same node.

17. The device of claim 15, the SMU connected to the internal node configured to source voltage and current and measure the associated current or voltage at the internal node.

18. The device of claim 15, the cascode structure formed by connecting the first MOSFET device and the second MOSFET device in series at the internal node.

* * * * *